United States Patent [19]
Moir et al.

[11] Patent Number: 6,066,629
[45] Date of Patent: May 23, 2000

[54] STORAGE STABLE AMOXYCILLIN AND CLAVULANATE SUSPENSION COMPOSITION

[75] Inventors: Peter Moir; Siobhan Greene, both of Clonmel, Ireland

[73] Assignee: Fuisz Technologies Ltd., Chantilly, Va.

[21] Appl. No.: 09/304,785

[22] Filed: May 4, 1999

[30] Foreign Application Priority Data

Feb. 26, 1999 [IE] Ireland ...................................... 990159

[51] Int. Cl.⁷ ..................................................... A61K 31/43
[52] U.S. Cl. .............................................................. 514/197
[58] Field of Search ................................................ 514/197

[56] References Cited

U.S. PATENT DOCUMENTS

| | | | |
|---|---|---|---|
| 4,301,149 | 11/1981 | Crowley | .................................. 424/114 |
| 4,441,609 | 4/1984 | Crowley | .................................. 206/204 |
| 4,537,887 | 8/1985 | Rooke et al. | .......................... 514/197 |
| 4,831,058 | 5/1989 | Pankhanis et al. | ..................... 514/570 |

FOREIGN PATENT DOCUMENTS

| | | | |
|---|---|---|---|
| WO 92/19227 | 11/1992 | WIPO | .............................. A61K 9/20 |
| WO 94/16696 | 8/1994 | WIPO | .............................. A61K 31/42 |
| WO 96/34605 | 11/1996 | WIPO | .............................. A61K 31/43 |

*Primary Examiner*—James H. Reamer
*Attorney, Agent, or Firm*—John F. Levis

[57] ABSTRACT

A dry powder formulation of antibiotic and β-lactam inhibitor is provided which is suitable for use in a liquid suspension.

17 Claims, No Drawings

STORAGE STABLE AMOXYCILLIN AND CLAVULANATE SUSPENSION COMPOSITION

FIELD OF THE INVENTION

The present invention relates to compositions containing antibiotics and β-lactam inhibitors, and more particularly, to improved storage-stable pharmaceutical dry powders containing amoxycillin and clavulanate, which when liquified are highly palatable and clinically effective against bacterial infections. The invention also relates to improved liquid suspensions of amoxycillin and clavulanate. In another form, the invention is further directed to a novel method for making formulations of amoxycillin and clavulanate which are suitable for use as pharmaceutical suspensions.

BACKGROUND OF THE INVENTION

β-lactames are enzymes which open the β-lactam ring of such antibiotics as penicillins and cephalosporins to yield products which are devoid of antibacterial activity. Clavulanic acid or 3-(β-hydroxyethylidene)-7-oxo-4-oxa-1-azabicyclo [3,2,0]heptane-2-carboxylic acid, including its pharmaceutically acceptable salts and esters, has now been well-recognized as a medium potency antibiotic which inhibits the production of β-lactame enzymes, thereby enhancing the efficacy of β-lactam antibiotics.

In particular, the combination of clavulanic acid and amoxycillin has been shown to be particularly effective against β-lactames. The latter antibiotic is usually combined in a relatively large weight excess with the clavulanic acid to yield various pharmaceutical compositions. Dry, unit-dose compressed tablets for oral administration are just one example of a suitable formulation. These are disclosed, for example, in WO 94/16696.

Unfortunately, in the preparation of many of these dry formulations the art has necessitated the inclusion of a complex formulation of excipients, including binders, glidants, disintegrants and even desiccants, etc. to yield a pharmaceutically acceptable carrier. This is in part due to the fact that clavulanate is a highly hygroscopic material which is highly unstable in aqueous media. Methods of formulation must therefore ensure that the product can retain its potency during storage, and yet can subsequently yield satisfactory dissolution rates. One such process is disclosed in WO 92/19227 and mandates the inclusion of both an intra-cellular and an extra-cellular disintegrant. Another process which is described in U.S. Pat. No. 4,537,887 specifies the inclusion of an edible desiccant within the composition itself. Other processes warrant the inclusion of a desiccant within a container housing the amoxycillin/clavulanate combination. In this regard, U.S. Pat. Nos. 4,301,149 and 4,441,609 are particularly salient.

Other preparations containing clavulanic acid derivatives and β-lactams include liquid pharmaceutical suspensions prepared from dry powder or granulate compositions. Liquid suspensions are often preferred from a dosing standpoint as these are often easier to administer and are more palatable than dry pills. Children and the elderly especially benefit from medication delivered in this form. Examples of such preparations may be found in WO 96/34605. Dry formulations containing the active ingredients are first prepared, and these are then liquified with water or other suitable liquid, either at the manufacturing facility, the pharmacy, or by the consumer just prior to ingestion. Unfortunately, some of these preparations are still not acceptable because of problems associated with the storage of these dry powder compositions. Many simply do not have a suitable shelf life to make them commercially viable. Some, for example, do not seek to optimize the type of preservative which stabilizes and extends the shelf life of the suspension.

What is now needed in the art is an improved pharmaceutical composition containing a β-lactam antibiotic such as amoxycillin and a β-lactamase inhibitor such as clavulanic acid (clavulanate) which is easy to manufacture, provides a potent combination of the two active agents, and yet is storage stable over extended periods, is easily liquified with a suitable aqueous carrier, is highly palatable, and is easily ingested.

SUMMARY OF THE INVENTION

These and other objects of the invention are provided by a pharmaceutical suspension composition comprising at least one β-lactam antibiotic in combination with at least one β-lactamase inhibitor, together with a pharmaceutically acceptable carrier. The composition may be in dry, powder form suitable for liquification or may comprise the liquid suspension prepared from the dry powder. As that term is used herein, "dry powder" refers to any formulation which is substantially dry and flowable, and can therefore include granules, flakes, dry spheroids and the like, as well as other dry forms which can be readily manufactured and may be subsequently dissolved or suspended in liquid, ingestible media. In its preferred form, the dry powder formulation of the invention optimizes the use of at least one alkyl hydroxy version of the benzoate ester, especially sodium methyl hydroxybenzoate and sodium propyl hydroxybenzoate.

Further included as part of the invention is a method of forming an antibiotic suspension formulation suitable for liquid suspension containing at least one β-lactam antibiotic together with at least one pharmaceutically acceptable form of at least one β-lactamase inhibitor. The method of manufacture comprises the step of adding at least one alkyl hydroxy version of a benzoic acid derivative, preferably benzoate, as a preservative. Also contemplated is the addition of a suitable ingestible aqueous liquid to the formulation so attained.

The invention also includes a method of dosing for infections which are normally treated with antibiotics and β-lactam inhibitors which comprises administering the novel liquid suspension formulations according to the various embodiments herein described.

DETAILED DESCRIPTION OF THE PREFERRED EMBODIMENTS

It has now been discovered that a pleasant-tasting and clinically efficacious pharmaceutical preparation may be prepared in the form of a suspension containing an effective amount of antibiotic and β-lactam inhibitor. The aqueous liquid suspension is prepared from a dry powder formulation containing the active ingredients. The dry powder composition is also part of the invention. The composition shows stability for extended periods due to the presence of at least one alkyl hydroxy version of a benzoic acid derivative such as benzoate, for example.

The novel composition contains as one active component at least one β-lactam antibiotic. The antibiotic is selected from the group consisting of penicillins and cephalosporins and their pharmaceutically acceptable compounds, including the salts, esters, aldehydes and ketone products thereof, as well as mixtures of any of the foregoing. Preferred is the penicillin known in the art as amoxycillin in a pharmaceutically acceptable form. Especially desirable is amoxycillin.

Even more preferred are the suitable salts and esters of amoxycillin, including amoxycillin trihydrate.

A second active component of the invention is at least one β-lactamase inhibitor. Of these, clavulanic acid or one of its pharmaceutically acceptable compounds such as the acceptable salts or esters thereof are preferred. Potassium clavulanate ($C_6H_8NO_5K$) is an especially preferred compound as the active component in the final formulation.

Any effective weight composition of the foregoing antibiotic(s) and β-lactam inhibitor(s) is desirable. An especially synergistic combination, however, will typically comprise an excess of antibiotic. Thus, a weight ratio of antibiotic to inhibitor will typically be within the range of about 10:1 to 1:1, more preferably about 6:1 to 1:1, and even more desirably about 5:1 to 3:1, with respect to the free forms of the respective compounds. In one particularly preferred embodiment, there will be about 4 parts antibiotic for every 1 part of inhibitor. Thus, an especially preferred combination will comprise about 4 weight parts of amoxycillin together with about 1 weight part of clavulanic acid derivative.

The actual weight amount of each of the foregoing active ingredients in the dry powder formulation will depend on the particular dosing regimen, e.g. how much of each of the particular compounds the skilled artisan wishes to include in the final dose. Another variable will also be the amount of aqueous liquid to be added to the dry powder to form the final liquid suspension.

Typically, the antibiotic and inhibitor will comprise about 0.1 to 90% by weight of the dry formulation. In certain embodiments it may be desirable to include about 0.5 to 10% of these bacterially active ingredients. It may be especially preferred to have a combination of antibiotic and β-lactamase inhibitor within the range of about 1% to 5%. On an actual weight basis, a typical dosing unit of the composition may contain about 25 to 2000 milligrams of antibiotic along with about 25 to 2000 milligrams of inhibitor, with respect to the free forms of the respective compounds. More preferably, there will be about 100 to 500 mg. of antibiotic for every 50 to 250 mg. of inhibitor. An especially preferred formulation of the composition of the invention will contain about 250 milligrams of antibiotic and about 62 milligrams of inhibitor in each unit dose. Another especially preferred formulation will have about 125 milligrams of antibiotic together with about 31 milligrams of β-lactam inhibitor. Suitably, formulations according to the invention will be provided in an amount such that the liquid suspension contains in about 2 to 10 ml, preferably in about 5 ml, a single unit dosage of antibiotic and Beta-lactam inhibitor. The foregoing weight and volume amounts may vary, of course, depending upon the particular dosage loading desired by the skilled artisan.

The active components heretofore described are formulated with a pharmaceutically acceptable carrier. Excipients known in the pharmaceutical industry may be utilized for this purpose. The carrier can therefore include, for example, one or more of the following: suspension aids, desiccants, diluents, stabilizers, glidants, binders, fillers and bulking agents, and the like. Suspension aids can include various gums, as for example xanthan gum. Since clavulanic acid derivatives, e.g. potassium clavulanate, are especially hygroscopic, it is particularly preferred to include some type of desiccant material together with this active, with additional amounts preferably included as part of the final suspension formulation as well. For this purpose, silicon dioxide (silica) in its colloidal and amorphous forms is especially suitable.

The filler material and bulking agents will typically comprise about 10 to 95% of the dry powder formulation. In a preferred embodiment, the filler(s) will make up about 60 to 85% of the formulation. Filler material can include any inert pharmaceutical bulking agent or material. Preferably, microcrystalline cellulose is utilized. Also highly efficacious is mannitol as a filler/bulking agent. Silicon dioxide also has excellent bulking properties. It is desirable that a combination of microcrystalline cellulose, mannitol and silicon dioxide be provided.

Also optionally included are one or more sweeteners, flavoring agents, and coloring agents in amounts of from about 0 to 5% of the final formulation. Sodium saccharin is desirable as a sweetener since it does not promote tooth decay. Other sweeteners may be chosen from the commercially available natural and synthetically derived products typically utilized in the confectionery and pharmaceutical industries. These may include, for example, mono-, di- and oligosaccharides, as well as aspartame, acesulfame and the like, including mixtures of any of the foregoing. Suitable flavoring agents include one or more commercially available fruit flavors, including cherry, grape, citrus and tutti-frutti flavors. These may be selected from known compounds typically available to the skilled artisan. Acid stabilizers such as sodium citrate and anhydrous citric acid may be also included to prevent breakdown of the various constituents in the suspension formulation.

It is especially desirable to include one or more preservatives in the dry formulation to help preserve both the dry composition and its liquid suspension version. The preservative component will typically comprise from about 0.01 to 2% of the dry formulation, and about 0.1 to 1% is even more desirable. Preferred for this purpose are one or more alkylhydroxybenzoate salts and esters. In particular, sodium methylhydroxy- and sodium propylhydroxybenzoate are contemplated. It has now been shown that the alkylhydroxybenzoate salts and esters are especially efficacious as preservatives. Two or more of these compounds are often particularly useful. These compounds are strongly preferred over their non-alkylhydroxylated versions, e.g. sodium benzoate. Sodium benzoate is not nearly as useful, and in certain embodiments has been demonstrated to have little or no utility as a preservative. It is especially desirable, therefore, to utilize both sodium methylhydroxybenzoate and sodium propylhydroxybenzoate as preservatives for the composition herein described. A highly efficacious ratio of the aforesaid methyl- to propyl-compounds will be within the range of about 6:1 to 1:1, more preferably about 4:1 to 2:1, and even more desirably will be within the range of about 3:1 by weight.

The foregoing components of the invention are admixed together in suitable commercial laboratory equipment to yield a dry, free-flowing powder. An appropriate dosing amount is then provided in a suitable dosing container. To this container is then added an ingestible aqueous liquid, and the final liquid suspension is thereby prepared. The liquid may be added by the druggist upon prescription, or by the consumer.

To prepare the final suspension formulation of the invention, the following procedure may be utilized: The active ingredients together with one or more additives or excipients heretofore described are first dry blended and then milled. These are then added to a fill bottle or other suitable container according to the particular dosing regimen. A suitable ingestible liquid is then added. Preferably, an aqueous liquid is utilized. More desirably, the liquid is water, but can include other ingestible aqueous liquid pharmaceutically compatible media known in the art. According to one embodiment, 25 grams of dry, prepared material according to the formulation set forth in Examples 1–3 below may be added to a suitable container to be mixed with 100 mL of liquid. Upon filling with liquid, 100 mL of suspension is yielded which can represent the equivalent of 20 doses, each of 5 mL and weighing approximately 550 mg.

The moisture content of the final dry suspension formulation is very low. The various embodiments herein set forth will have a moisture content not exceeding about 10% (by weight). Even more desirably, the final moisture content will not exceed about 8%, and even more preferably will not be in excess of about 6%, or even lower. For this reason, the dry formulations are highly storage stable for extended periods. In this regard, they successfully inhibit the growth of various microorganisms, and are thereby meet the criteria set forth in various pharmacopeia. Upon dilution with the appropriate liquid, they are fully potent according to their stated dosage. The unique formulation of the invention is also highly storage stable once formed into its corresponding liquid suspension for the period of time necessary to dose.

EXAMPLES

The following examples illustrate various embodiments of the invention. These should not be construed as limiting the scope thereof however.

Example 1

TABLE 1 indicates quantitatively (in milligrams—mg.) the composition for each of three suspensions (Examples 1, 2 and 3). The fourth column is included for comparative purposes (Example 4), and was done on a bottle fill weight basis and standardized for fill weight. (Numerical figures in headings represent ratio of Amoxycillin:Clavulanic Acid).

TABLE 1

| Formulation (mg./bottle) | Example 1 250/62 mg | Example 2 125/62 mg | Example 3 125/31 mg | Example 4 125/31 mg |
|---|---|---|---|---|
| Amoxycillin Trihydrate Powder | X | X | X | X |
| Potassium Clavulanate/Syloid Al-1-FP (1:1) | XX | XX | XX | XX |
| Sodium Saccharin E.P. | 105 | 105 | 47 | 105.75 |
| Na Methyl Hydroxy Benzoate BP | 75 | 75 | 33.3 | 75 |
| Na Propyl Hydroxy Benzoate BP | 25 | 25 | 11 | 24.75 |
| Na Citrate Anhydrous Powder BP | 165 | 165 | 73 | 165 |
| Citric Acid Anhydrous Powder BP | 42.5 | 42.5 | 18.9 | 42.5 |
| Xanthan Gum EP | 192.3 | 193.3 | 85.5 | 192.4 |
| Cherry Flavor | 77.5 | 77.5 | 34.4 | 77.4 |
| Amorphous $SiO_2$ EP (Aerosil 200) | 332.5 | 332.5 | 147.7 | 332.3 |
| Colloidal $SiO_2$ EP (AL-1-FP) | 4192.5 | 4192.5 | 1863.0 | 4192.0 |
| Microcrystalline Cellulose (Avicel pH 112) E.P. | 812.5 | 812.5 | 361 | 812.25 |
| Mannitol | to 25000 | to 25000 | to 11000 | to 25000 |
|  | fill wt. = 25 g | fill wt. = 25 g | fill wt. = 11 g | fill wt. = 25 g |

X = potency dependent, ~3% overage on Amoxycillin.
XX = potency dependent, and a ~3% overage is included on Clavulanic Acid.
Sodium methylhydroxybenzoate was sourced as NIPAGIN M SODIUM, while sodium propylhydroxybenzoate was sourced as NIPASOL M SODIUM.

Final fill volume for each of the formulations in TABLE 1 was 100 mL, representing 20 doses of 5 mL.

Example 2

In this example, a storage stability study was conducted with a dry powder comparative example vs. the dry powder formulation as set forth in the invention. The results are indicated, respectively, in Tables 2A and 2B below. The formulations were identical, with the exception that TABLE 2A utilized 0.16% sodium benzoate as a preservative, while TABLE 2B utilized 0.3% sodium methylhydroxybenzoate and 0.1% of sodium propylhydroxybenzoate as preservatives. The formulation of TABLE 2B was furthermore identical to the formulation set forth in Example 1 for 125 mg/62 mg, respectively, of amoxycillin and clavulanate:

TABLE 2A

| CO-AMOXICLAV SUSPENSION - COMPARATIVE FORMULATION STRENGTH 125-62 | | | | | | |
|---|---|---|---|---|---|---|
| Inoculum ATCC Lab No R2909 | Pseudomonas Aeruginosa ATCC 9027 | Escherichia coli ATCC 8739 | Staphylococcus aureus ATCC 6538 | Candida albicans ATCC 10231 | Aspergillus niger ATCC 16404 | Zygosaccharomyces rouxii ATCC 28253 |
| Time Initial | $2.9 \times 10^5$ | $3.2 \times 10^5$ | $3.4 \times 10^5$ | $2.2 \times 10^5$ | $3.5 \times 10^5$ | $2.1 \times 10^5$ |
| 6 Hours | <10 | <10 | <10 | $9.5 \times 10^3$ | $1.2 \times 10^4$ | $3.1 \times 10^4$ |
| 24 Hours | <10 | <10 | <10 | $8.8\ 10^3$ | $7.4 \times 10^3$ | $2.1 \times 10^4$ |
| 7 Days | <10 | <10 | <10 | $4.8 \times 10^4$ | $3.2 \times 10^4$ | $5.2 \times 10^4$ |
| 14 Days | <10 | <10 | <10 | $5.4 \times 10^5$ | $5.6 \times 10^4$ | $8.1 \times 10^4$ |

TABLE 2A-continued

CO-AMOXICLAV SUSPENSION - COMPARATIVE FORMULATION STRENGTH 125-62

| Inoculum ATCC Lab No R2909 | Pseudomonas Aeruginosa ATCC 9027 | Escherichia coli ATCC 8739 | Staphylococcus aureus ATCC 6538 | Candida albicans ATCC 10231 | Aspergillus niger ATCC 16404 | Zygosaccharomyces rouxii ATCC 28253 |
|---|---|---|---|---|---|---|
| 21 Days | <10 | <10 | <10 | $2.4 \times 10^6$ | $9.6 \times 10^5$ | $1.2 \times 10^5$ |
| 28 Days | <10 | <10 | <10 | $1.8 \times 10^7$ | $2.6 \times 10^6$ | $8.2 \times 10^5$ |

Conclusion:
The above formulation DOES NOT MEET the EP:A specifications for Preservative Systems
The above formulation DOES NOT MEET the EP:B specifications for Preservative Systems

TABLE 2A

CO-AMOXICLAV SUSPENSION - NEW FORMULATION BATCH

| Innoculum ATCC Lab No: R3355 | Pseudomonas aeruginosa ATCC 9027 | Escherichia coli ATCC 8739 | Staphylococcus aureus ATCC 6538 | Candida albicans ATCC 10231 | Aspergillus niger ATCC 16404 | Zygosaccharomyces rouxii ATCC 28253 |
|---|---|---|---|---|---|---|
| Time Initial | $5.5 \times 10^5$ | $1.9 \times 10^5$ | $3.1 \times 10^5$ | $2.5 \times 10^5$ | $1.6 \times 10^5$ | $2.2 \times 10^2$ |
| 7 Days | <10 | <10 | <10 | $8.6 \times 10^2$ | $1.1 \times 10^2$ | $2.6 \times 10^2$ |
| 14 Days | <10 | <10 | <10 | <10 | $9.0 \times 10^1$ | <10 |
| 21 Days | <10 | <10 | <10 | <10 | $8.0 \times 10^1$ | <10 |
| 28 Days | <10 | <10 | <10 | <10 | $3.0 \times 10^1$ | <10 |

Conclusion: The above formulation MEETS the European Pharmacopoeia specifications for Preservative Systems It is expected that certain changes or modifications to the invention herein described may be effected by those skilled in the art without departing from the true spirit and scope thereof as set forth in the claims and the accompanying specification.

What is claimed is:

1. A dry powder pharmaceutical suspension composition suitable for use as a liquid suspension comprising at least one β-lactam antibiotic in combination with at least one β-lactamase inhibitor, together with a pharmaceutically acceptable carrier, said composition further comprising at least one preservative which is selected from the group consisting of the alkylhyroxybenzoates.

2. The composition of claim 1, wherein said antibiotic is at least one member selected from the group consisting of penicillins and cephalosporins and the pharmaceutically acceptable versions thereof, and said inhibitor comprises clavulanic acid, its pharmaceutical salts, esters, aldehydes and ketone products thereof.

3. The composition of claim 2, wherein said antibiotic is amoxycillin, its pharmaceutically acceptable salts and esters.

4. The composition of claim 3, wherein said amoxycillin is amoxycillin trihydrate and said inhibitor is potassium clavulanate.

5. The composition of claim 2, wherein said pharmaceutically acceptable carrier is at least one additive selected from the group consisting of suspension aids, desiccants, diluents, stabilizers, glidants, binders, fillers and bulking agents.

6. The composition of claim 5, wherein said suspension aid is xanthan gum and said bulking agent is mannitol.

7. The composition of claim 2, said composition having a weight ratio of antibiotic to inhibitor within the range of from about 10:1 to 1:1.

8. The composition of claim 7, wherein said composition has a weight ratio within the range of about 4:1 to 1:1.

9. The composition of claim 8, wherein said composition has a weight ratio within the range of about 2:1 to 1:1.

10. The composition of claim 2, wherein said alkylhydroxybenzoate is at least one member selected from the group consisting of methylhydroxybenzoate and propylhydroxybenzoate.

11. The composition of claim 10, wherein said alkylhydroxybenzoate is a combination of methylhydroxybenzoate and propylhydroxybenzoate.

12. The composition of claim 11, wherein said composition comprises substantially no sodium benzoate.

13. The composition of claim 12, wherein the weight ratio of said methylhydroxybenzoate to said propylhydroxybenzoate is in the range of about 6:1 to 1:1.

14. A method of forming a dry powder pharmaceutical formulation suitable for use as a liquid suspension, comprising:

1) combining in admixture at least one antibiotic and at least one β-lactamase inhibitor in weight excess of antibiotic;

2) further admixing one or more ingredients selected from the group consisting of suspension aids, desiccants, fillers, sweeteners and flavorants, and at least one preservative selected from the group consisting of sodium methylhydroxybenzoate and sodium propylhydroxybenzoate.

15. The method of claim 14, wherein said antibiotic is amoxycillin and said inhibitor is a derivative of clavulanic acid.

16. The method of claim 15, wherein said amoxycillin and said inhibitor are combined in weight ratios of within the range of about 4:1 and about 2:1, and further wherein said preservative is a combination of sodium methylhydroxybenzoate and sodium propylhydroxybenzoate in a weigh ratio of about 4:1 to 2:1.

17. The product prepared according to the method of claim 14.

* * * * *